(12) United States Patent
Gonopolskiy et al.

(10) Patent No.: US 8,831,699 B2
(45) Date of Patent: *Sep. 9, 2014

(54) PHYSIOLOGICAL SENSOR WITH A TAIL

(71) Applicant: Covidien LP, Mansfield, MA (US)

(72) Inventors: Oleg Gonopolskiy, West Bloomfield, MI (US); Melissa Muto, Royal Oak, MI (US); Matthew Stimpson, Macomb, MI (US); Richard Morabito, Grosse Ile, MI (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/023,657

(22) Filed: Sep. 11, 2013

(65) Prior Publication Data

US 2014/0012107 A1   Jan. 9, 2014

Related U.S. Application Data

(63) Continuation of application No. 12/860,444, filed on Aug. 20, 2010, now Pat. No. 8,560,035.

(60) Provisional application No. 61/235,505, filed on Aug. 20, 2009.

(51) Int. Cl.
    *A61B 5/00* (2006.01)
(52) U.S. Cl.
    USPC ......................................................... 600/323
(58) Field of Classification Search
    USPC ......................................................... 600/323
    See application file for complete search history.

(56) References Cited

U.S. PATENT DOCUMENTS

| 6,519,484 | B1 * | 2/2003 | Lovejoy et al. | 600/323 |
| 6,745,061 | B1 * | 6/2004 | Hicks et al. | 600/344 |
| 8,560,035 | B2 * | 10/2013 | Gonopolskiy et al. | 600/323 |
| 2004/0039272 | A1 * | 2/2004 | Abdul-Hafiz et al. | 600/322 |
| 2005/0197550 | A1 * | 9/2005 | Al-Ali et al. | 600/323 |
| 2005/0251004 | A1 * | 11/2005 | Istvan et al. | 600/395 |
| 2006/0084852 | A1 * | 4/2006 | Mason et al. | 600/344 |
| 2007/0197886 | A1 * | 8/2007 | Naganuma et al. | 600/322 |
| 2007/1019788 | | 8/2007 | Naganuma et al. | |
| 2008/0242958 | A1 * | 10/2008 | Al-Ali et al. | 600/323 |
| 2009/0143657 | A1 * | 6/2009 | Diab et al. | 600/344 |
| 2009/0182209 | A1 * | 7/2009 | Benni | 600/323 |
| 2010/0049018 | A1 * | 2/2010 | Duffy et al. | 600/323 |
| 2011/0046463 | A1 | 2/2011 | Gonopolskiy et al. | |
| 2012/0046530 | A1 * | 2/2012 | Al-Ali et al. | 600/310 |

* cited by examiner

*Primary Examiner* — Rodney Fuller
(74) *Attorney, Agent, or Firm* — Harness, Dickey & Pierce, PLC

(57) ABSTRACT

An exemplary sensor includes a sensor pad defining a plurality of openings and a circuit board. The circuit board is at least partially disposed in the sensor pad and has a light source configured to generate near-infrared light and a light detector configured to receive near-infrared light. The light source and the light detector are each aligned with one of the openings of the sensor pad so that near-infrared light generated by the light source can travel through a part of a patient's body to the light detector and the near-infrared light received by the light detector indicates oxygen saturation of the part of the patient's body through which the light travelled. The circuit board further includes an integrally formed tail at least partially disposed in the sensor pad. Additionally, the sensor pad includes an overlay disposed on the tail.

12 Claims, 3 Drawing Sheets

PHYSIOLOGICAL SENSOR WITH A TAIL

CROSS-REFERENCE TO RELATED APPLICATIONS

This application is a continuation application of U.S. Ser. No. 12/860,444 filed on Aug. 20, 2010, which claims priority to U.S. Ser. No. 61/235,505 filed Aug. 20, 2009, the contents of which are incorporated herein by reference in their entirety.

BACKGROUND

Near-infrared sensors are used in the medical industry to measure the amount of oxygen saturation in a patient's blood or tissue. A cable is used to connect the sensor to a controller that controls operation of the sensor and receives signals from the sensor. Sometimes, patients move while wearing the sensor. For instance, a clinician may move the patient (e.g., rotate the patient) during a procedure. This movement could either cause the sensor to disconnect from the cable or cause the patient discomfort due to lying on the cable. Accordingly, a near-infrared sensor is needed that allows the patient to be moved or rotated without the risk of disconnecting the sensor from the cable or the discomfort caused by lying on the cable.

DETAILED DESCRIPTION

An exemplary physiological sensor that allows a patient to be moved without significant risk of disconnecting the sensor from a cable or causing the patient discomfort from lying on the cable includes a sensor pad housing a circuit board. The circuit board has an integrally formed tail and the sensor pad includes an overlay that is disposed on the tail. The tail and overlay have a thickness that is less than a thickness of the cable. Further, both the tail and overlay are flexible, and the overlay includes a soft, slippery material. The tail has a length that is sufficient so that the sensor will not be disconnected from the cable if the patient is rotated. Moreover, should the patient be rotated to lie on the tail and overlay, the patient will experience a reduced level of discomfort than if the patient were to lie on the cable.

The sensor pad further houses a light source configured to generate near-infrared light and a light detector configured to receive near-infrared light. The light source and the light detector are each aligned with one of the openings of the sensor pad so that near-infrared light generated by the light source can travel through a part of a patient's body to the light detector and the near-infrared light received by the light detector indicates oxygen saturation of the part of the patient's body through which the light travelled.

Figure 1:
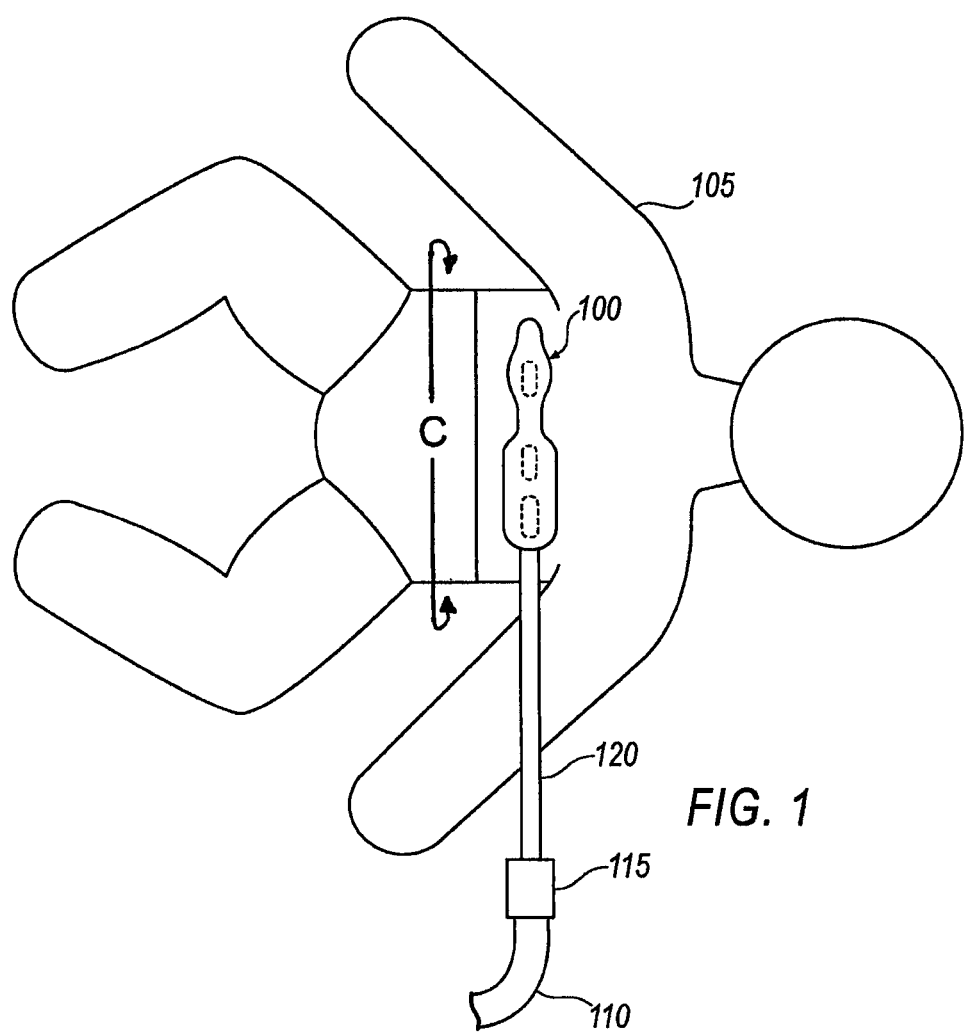
FIG. 1 illustrates a sensor having a tail and disposed on a patient.

FIG. 1 illustrates an exemplary sensor 100 that allows a patient to be moved without the risk of disconnecting the cable from the sensor or the discomfort caused by lying on a cable. The sensor 100 may take many different forms and include multiple and/or alternate components and facilities. While an exemplary sensor 100 is shown, the exemplary components illustrated in the figures are not intended to be limiting. Indeed, additional or alternative components and/or implementations may be used.

As illustrated in FIG. 1, the sensor 100 may be disposed on a patient 105 and connect to a cable 110 via a connector 115. The sensor 100 includes a tail 120 that provides adequate distance between the patient 105 and the connector 115 and cable 110, which reduces the likelihood that the patient 105 will lie on the connector 115 or cable 110 if the patient 105 is rotated. Further, because the tail 120 is thinner than the connector 115 and cable 110, the patient 105 can lie on the tail 120 without the discomfort that comes with lying directly on the connector 115 or cable 110. Additionally, the tail 120 provides sufficient slack that the patient 105 can be rotated away from the connector 115 without a significant risk that doing so will disconnect the sensor 100 from the cable 110.

In one exemplary approach, the length of the tail 120 may be at least approximately three-fourths the circumference C of a region of a patient's body to which the sensor is applied, such as, for example, the patient's waist. For instance, if the circumference C of a patient's waist is approximately 7 inches (common in prematurely born patients 105), the tail 120 may be at least approximately 5.25 inches long. Of course, this formula for the length of the tail 120 is merely exemplary and other formulas for determining the length may be used. Indeed, the tail 120 is not necessarily drawn to scale in the figures. Therefore, while the tail 120, in one exemplary approach, may be three-fourths the circumference C of the patient's waist, the exemplary sensors 100 shown in FIGS. 1-8 do not necessarily correspond with that formula for ease of illustration and to evidence that the tail 120 may have other lengths than this exemplary formula suggests.

Different tail 120 lengths may be used with different patients 105. For example, different sensors 100 may have tail 120 lengths corresponding to different types of patients, such as premature neonates, infants, toddlers, children, teenagers, or adults. Further, the tail 120 length of the sensor 100 may include further designations, such as small, medium, large, or extra large, etc. based on the circumference of the patient's waist as related to a percentile range. For instance, a sensor 100 with a small tail 120 may be used with patients 105 with waist circumferences C in the 0-30 percentile range, a sensor 100 with a medium tail 120 may be used with those patients 105 whose waist circumference C are in the 30-70 percentile range, a sensor 100 with a large tails 120 may be used with a patient 105 whose waist circumference C is in the 70-90 percentile, and a sensor 100 with an extra large tail 120 may be used with a patient 105 with a waist circumference C in the 90-99 percentile. Thus, clinicians may be able to choose the sensor 100 with the appropriate tail size for the patient 105 based on the circumference C of the patient's waist. By way of example, a clinician treating an infant patient 105 with a waist having a circumference C in the 50$^{th}$ percentile may choose an infant sensor with a medium sized tail. A clinician would use a sensor 100 with a larger tail for an infant patient with a waist circumference C that is in the 80$^{th}$ percentile.

The sensor 100 further includes a sensor pad 125 housing a light source 130 and a light detector 135. The light source 130 is configured to generate near-infrared light and transmit the generated near-infrared light into a part of the patient's body 105. The light source 130 may include a light emitting diode (LED), a laser diode, or any other device capable of generating near-infrared light. The light detector 135 may include any device capable of detecting the near-infrared light generated by the light source 130 after the light has been transmitted through part of the patient's body 105. For instance, the light detector 135 may include a photodiode. The light detector 135 is further configured to generate a signal that represents the near-infrared light detected. The light source 130 and light detector 135 may each be aligned with an opening 140 in the sensor pad 125 (see FIG. 2). This way, light generated by the light source 130 may travel into the patient's body 105 and be received at the light detector 135. The sensor pad 125 may house any number of light sources 130 and light detectors 130. For instance, the sensors 100 illustrated in FIGS. 2-5 include one light source 130 and two light detectors 130.

The connector 115 may include any device capable of interfacing the sensor 100 with the cable 110. For instance, one end of the interface may be configured to receive an end of the tail 120 while another end of the interface may be configured to receive the cable 110. The cable 110 may include a group of wires that connect the sensor 100. The wires in the cable no may transmit control signals from the controller (not shown) to the light source 130 and light detector 135. Moreover, the cable no may transmit signals representative of oxygen saturation from the light detector 135 to the controller.

Figure 2:
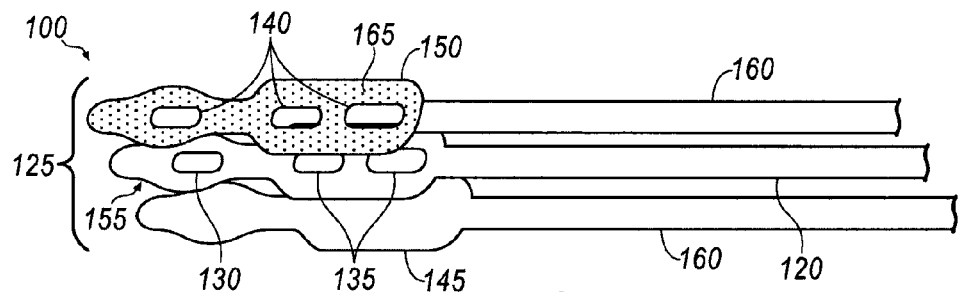
FIG. 2 illustrates an assembly view of an exemplary sensor having a sensor pad with layers and a circuit board with an integrally formed tail.

Referring to FIG. 2, the sensor pad 125 includes a top layer 145 and a bottom layer 150. Also, the sensor pad 125 houses a circuit board 155. The light source 130 and light detector 135 are disposed on the circuit board 155, and the tail 120 is integrally formed with the circuit board 155. Further, the sensor pad 125 includes an overlay 160 that, in one exemplary approach, is integrally formed with the top layer 145, the bottom layer 150, or both. The tail 120 is at least partially disposed within the overlay 160.

The sensor pad 125 may include a flexible material such as a foam or elastic material. One or both of the top layer 145 and the bottom layer 150 may be at least partially formed from the flexible material, which allows the sensor pad 125 to bend to fit the contours of the patient's body 105. In FIG. 2, the overlay 160 is formed from the top layer 145 and the bottom layer 150 and is configured to be at least partially disposed about the tail. When the patient 105 is rotated, the patient 105 may lie on the overlay 160. Accordingly, the material from which the top and bottom layers 145, 150 are formed may be soft in addition to flexible. Moreover, the material from which the top layer 145 and bottom layer 150 are formed may be slippery to prevent or reduce abrasions on the patient's skin 105 caused by the overlay 160 rubbing against the patient 105. In one exemplary implementation, both the tail 120 and the overlay 160 are substantially flat so that the thickness of the tail 120 and overlay 160 do not cause significant discomfort should the patient 105 be rotated to lie on the tail 120 and overlay 160.

The bottom layer 150 may define openings 140 that allow near-infrared light generated by the light source 130 to travel through part of the patient 105 and be received by the light detector 135. The bottom layer 150 may include an adhesive 165, such as a pressure sensitive adhesive 165, that allows the sensor pad 125 to adhere to the patient 105. This way, the sensor pad 125 may remain in a fixed location relative to the patient 105. The top layer 145 may be opaque (i.e., formed from a light-blocking material) to prevent ambient or other forms of interfering light from interfering with the light detector 135.

The circuit board 155 may be flexible so that the circuit board 155 may fit the contours of the patient's body 105 along with the sensor pad 125. For instance, the circuit board 155 may be a flexible printed circuit board that includes the light source 130, light detector 135, and traces (not shown) that allow signals to be transmitted to and from the controller (not shown) via the connector 115 and cable 110. In one exemplary approach, the connector 115 electrically connects the wires in the cable 110 to the traces printed on the tail 120 to allow signal communication between the controller and the sensor 100.

Figure 3:
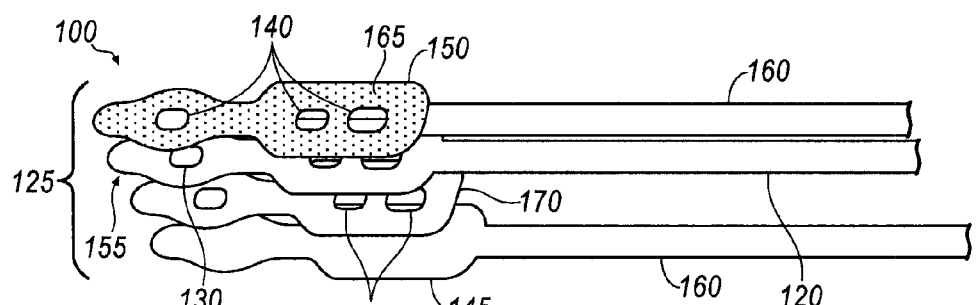
FIG. 3 illustrates an assembly view of an exemplary sensor having a sensor pad that includes a spacer and a circuit board with an integrally formed tail.

FIG. 3 illustrates another exemplary sensor 100 having the tail. In this exemplary approach, the sensor pad 125 further includes a spacer 170 disposed between the top layer 145 and the bottom layer 150. In particular, the spacer 170 is disposed between the top layer 145 and the circuit board 155. The spacer 170 may be used to smooth bumps in the sensor pad 125 caused by, for instance, the height of the light source 130 and/or light detector 135. Like the top layer 145 and bottom layer 150, the spacer 170 may be formed from a flexible material. As illustrated, the spacer 170 does not extend over the tail. However, one exemplary implementation may include forming the spacer 170 in a way that does extend over the tail 120 (i.e., between the tail 120 and the overlay 160).

Figure 4:
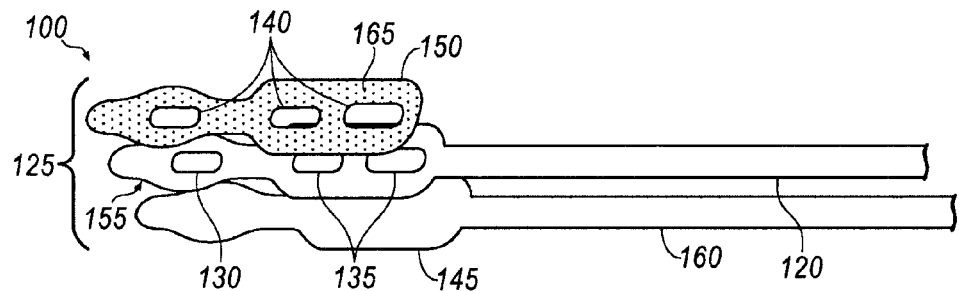
FIG. 4 illustrates an assembly view of an exemplary sensor having a sensor pad with a bottom layer that forms an overlay disposed on a tail that is integrally formed with a circuit board.
Figure 5:
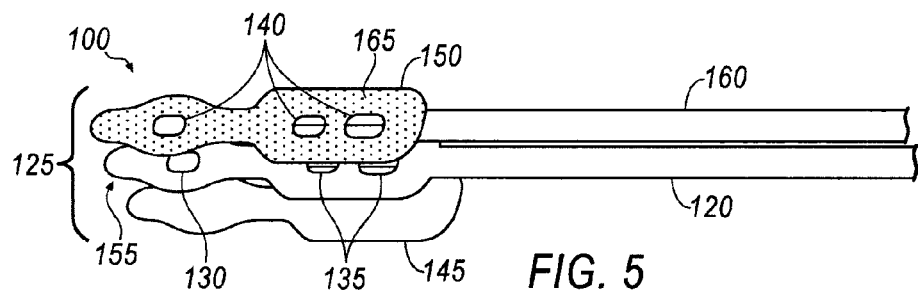
FIG. 5 illustrates an assembly view of an exemplary sensor having a sensor pad with a top layer that forms an overlay disposed on a tail that is integrally formed with a circuit board.

FIG. 4 illustrates an exemplary sensor 100 where the overlay 160 is formed by the top layer 145 but not the bottom layer 150. FIG. 5 illustrates an exemplary sensor 100 where the overlay 160 is formed by the bottom layer 150 but not the top layer 145. Using only one layer of the sensor pad 125 (i.e., only the top layer 145 or the bottom layer 150) may reduce manufacturing costs as well as the thickness of the overlay 160.

Figure 6:
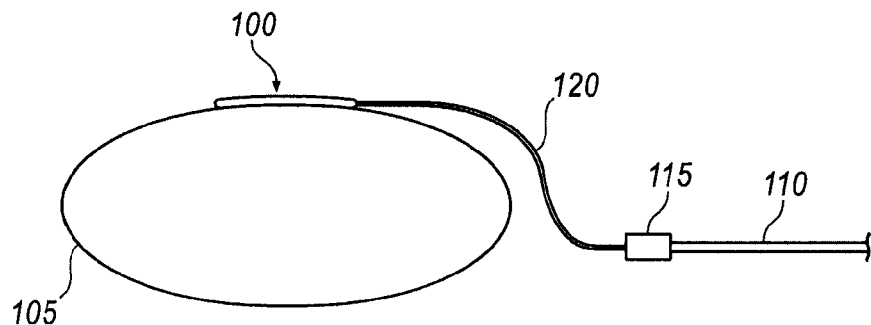
FIG. 6 illustrates an exemplary sensor having a tail and disposed on a patient's body.
Figure 7:
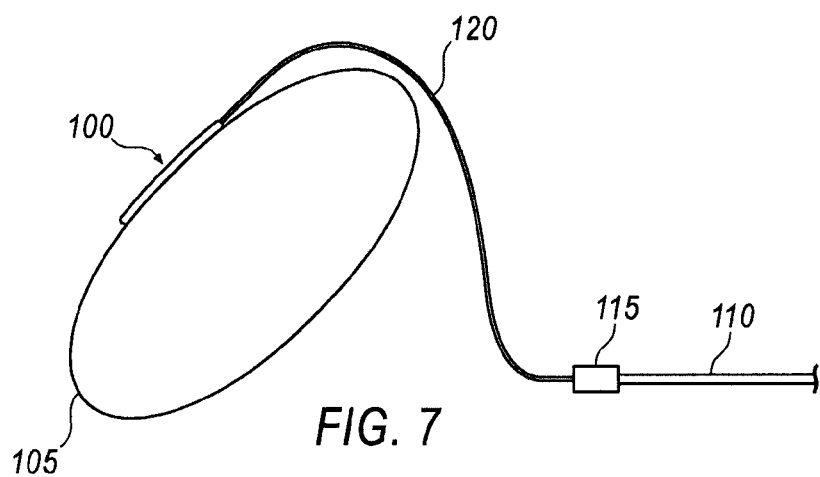
FIG. 7 illustrates an exemplary sensor having a tail and disposed on a rotated patient's body.
Figure 8:
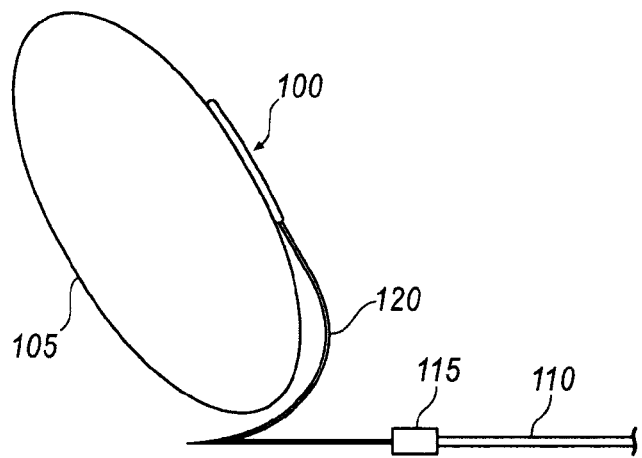
FIG. 8 illustrates an assembly view of an exemplary sensor having a tail and disposed on a rotated patient such that the patient is lying on the tail.

FIGS. 6-8 illustrate exemplary sensors 100 disposed on patients 105 in various orientations. FIG. 6 illustrates an exemplary sensor 100 disposed on a patient 105 lying on, for example, his or her back with the sensor 100 adhered to the patient's torso 105. The tail 120 provides a sufficient distance between the connector 115 and the cable 110 so that the patient 105 can be rotated without lying on the connector 115, the cable no, or both.

FIG. 7 illustrates an exemplary sensor 100 disposed on a rotated patient 105. Here, the patient 105 is rotated in a direction away from the connector 115. The tail 120 has a sufficient length that the sensor 100 remains connected to the connector 115 despite the rotation of the patient 105. That is, the tail 120 gives the sensor 100 some slack so that the patient 105 may be rotated without disconnecting the sensor 100 from the connector 115 and cable 110. Therefore, the sensor 100 may continue to communicate with the controller (not shown) via the cable 110 and connector 115 while the patient 105 is rotated away from the connector 115.

FIG. 8 illustrates an exemplary sensor 100 disposed on a patient 105 who is rotated toward the connector 115 and cable 110. The length of the tail 120 is sufficient that the patient 105 will roll onto the tail 120 and not the connector 115 and cable 110. Because the tail 120 is thinner than the connector 115 and the cable no, lying on the tail 120 does not cause the patient 105 significant discomfort. Moreover, the overlay 160 includes a soft material that further reduces discomfort. As previously discussed, the overlay 160 may further be slippery to reduce the risk of abrasions caused by the tail 120 rubbing against the patient's skin 105.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the invention is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A sensor comprising:
   a sensor pad portion having a first layer and a second layer;
   a generally planar circuit board disposed between said first layer and said second layer, said circuit board having a light source configured to generate near-infrared light and a light detector configured to receive said near-infrared light after it has penetrated into and been reflected from a patient's body; and
   an elongated tail portion having a tail that is integrally formed with said circuit board, said tail being disposed between a first overlay and a second overlay over substantially the full length of the tail portion.

2. The sensor of claim 1, wherein said tail portion is configured to connect said sensor pad portion to a cable.

3. The sensor of claim 2, wherein said tail portion is substantially planar and a height of said tail portion is less than the height of said cable when said cable is lying on a flat surface.

4. A sensor as set forth in claim 1, wherein the tail portion has a length that is at least three-fourths of a circumference of the patient's waist.

5. A sensor as set forth in claim 1, wherein the tail is flexible.

6. A sensor as set forth in claim 1, wherein the circuit board includes a flexible printed circuit board.

7. The sensor of claim 1, wherein said first and second overlays are integrally formed with said first and second layers, respectively.

8. A sensor comprising:
   a sensor pad portion having a first layer and a second layer;
   a generally planar circuit board disposed between said first layer and said second layer, said circuit board having a light source configured to generate near-infrared light and a light detector configured to receive said near-infrared light after it has penetrated into and been reflected from a patient's body;
   an elongated tail portion having a tail that is integrally formed with said circuit board and that is configured to connect said sensor pad portion to an electrical cable;
   wherein said tail portion is substantially flat and has a length that is at least three-fourths of a circumference of the patient's waist.

9. The sensor of claim 8, wherein a height of said tail portion is less than a height of said cable when said cable is lying on a flat surface.

10. A sensor as set forth in claim 8, wherein said circuit board is flexible.

11. The sensor of claim 8, wherein said tail is disposed between a first overlay and a second overlay over substantially the full length of the tail portion.

12. The sensor of claim 11, wherein said first and second overlays are integrally formed with said first and second layers, respectively.

* * * * *